United States Patent [19]

Murdock, III

[11] Patent Number: 4,740,706

[45] Date of Patent: * Apr. 26, 1988

[54] SANITIZER FOR BATHROOM ARTICLES

[75] Inventor: James O. Murdock, III, West Palm Beach, Fla.

[73] Assignee: Murdock Laboratories, Inc., West Palm Beach, Fla.

[*] Notice: The portion of the term of this patent subsequent to Nov. 25, 2003 has been disclaimed.

[21] Appl. No.: 844,155

[22] Filed: Mar. 26, 1986

Related U.S. Application Data

[63] Continuation-in-part of Ser. No. 721,659, Apr. 10, 1985.

[51] Int. Cl.$^4$ ................................................ A61L 2/10
[52] U.S. Cl. .................................. 250/455.1; 422/24; 422/300; 312/204
[58] Field of Search ............... 250/455.1, 454.1, 453.1; 422/24, 300, 291; 312/209

[56] References Cited

U.S. PATENT DOCUMENTS 4,625,119 11/1986 Murdock .......................... 250/455.1

Primary Examiner—Craig E. Church
Assistant Examiner—Jack I. Berman
Attorney, Agent, or Firm—Cushman, Darby and Cushman

[57] ABSTRACT

A sanitizer for bathroom articles such as toothbrushes includes a closeable housing having a rotatable rack therein for receiving the bathroom article, a sanitizing element such as a germicidal lamp within the housing to sanitize the bathroom article, and a drainage diaphragm located beneath the bathroom article to receive precipitated drainage fluid therefrom (under the force of gravity) and direct the same towards the peripheral portions of the housing due to the concave shape of the drainage diaphragm. Drainage holes located in the peripheral area of the housing pass drainage fluid from the housing directed thereto. Adjunct electrical devices, such as a radio, clock or a calculator may be contained within the housing.

23 Claims, 7 Drawing Sheets

FIG. 1
FIG. 7
FIG. 4
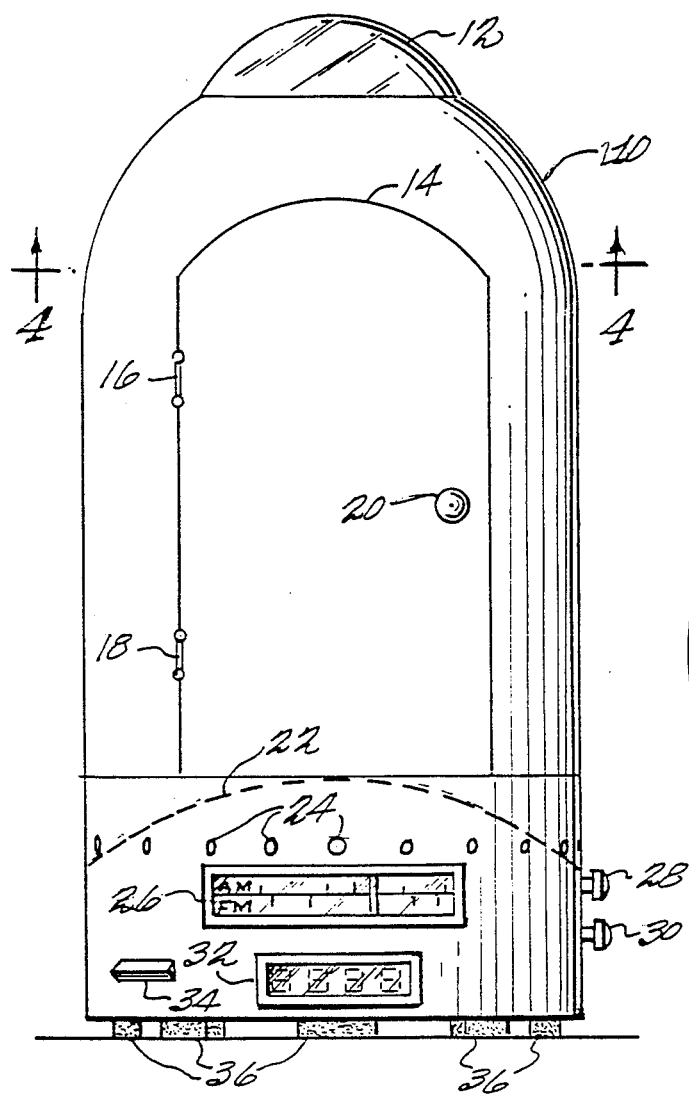
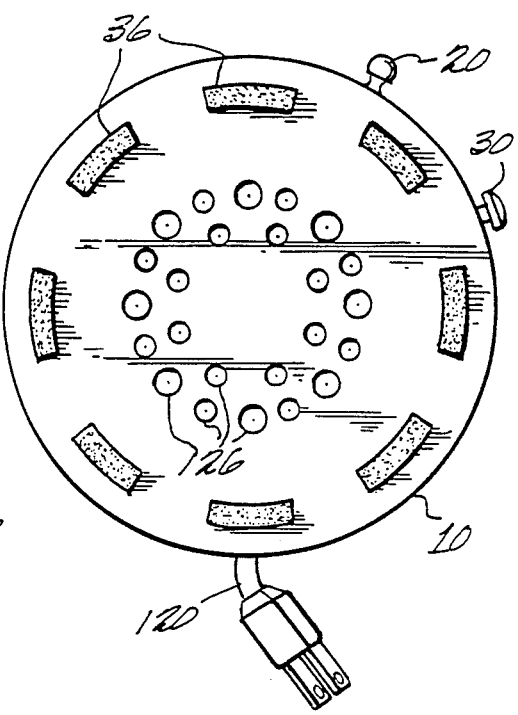
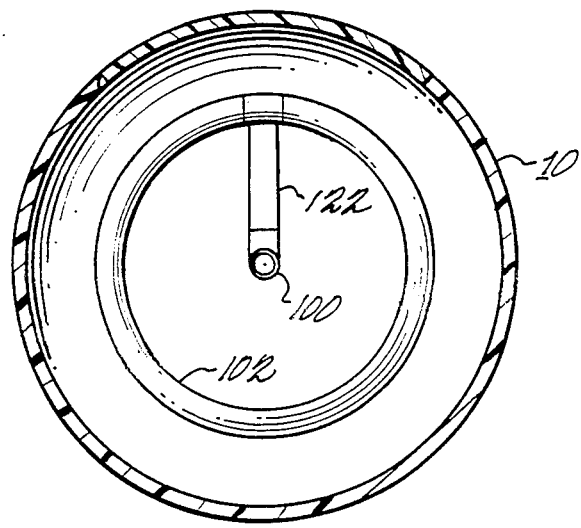

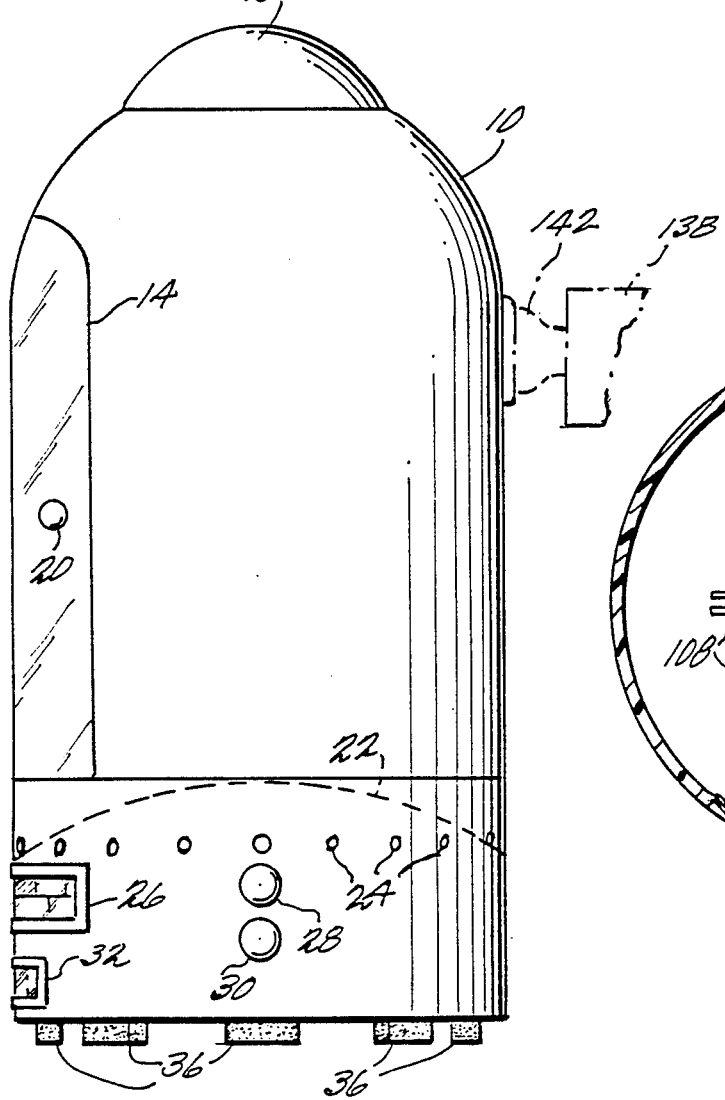
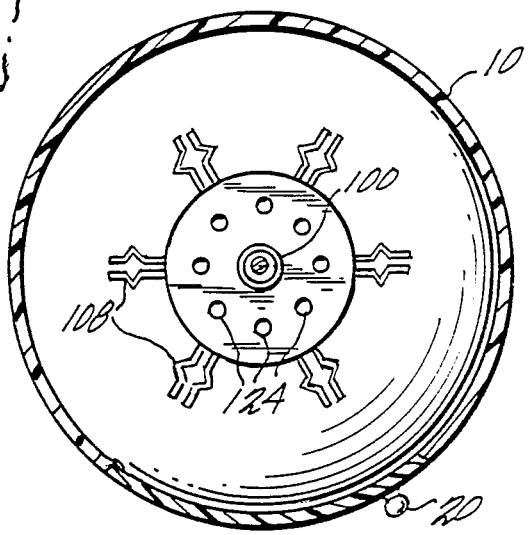
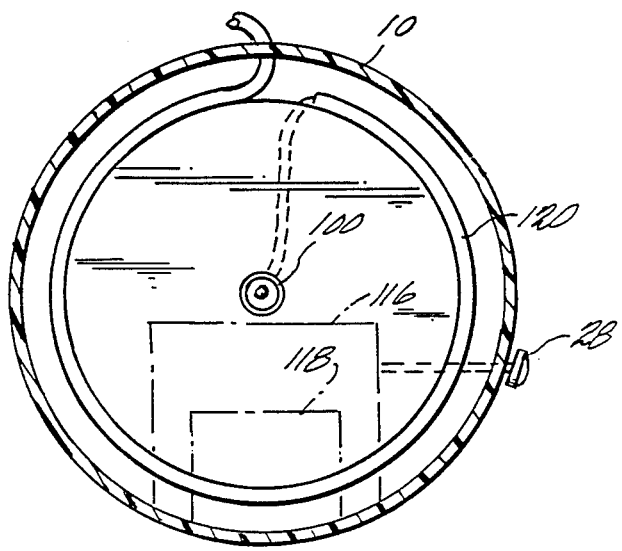

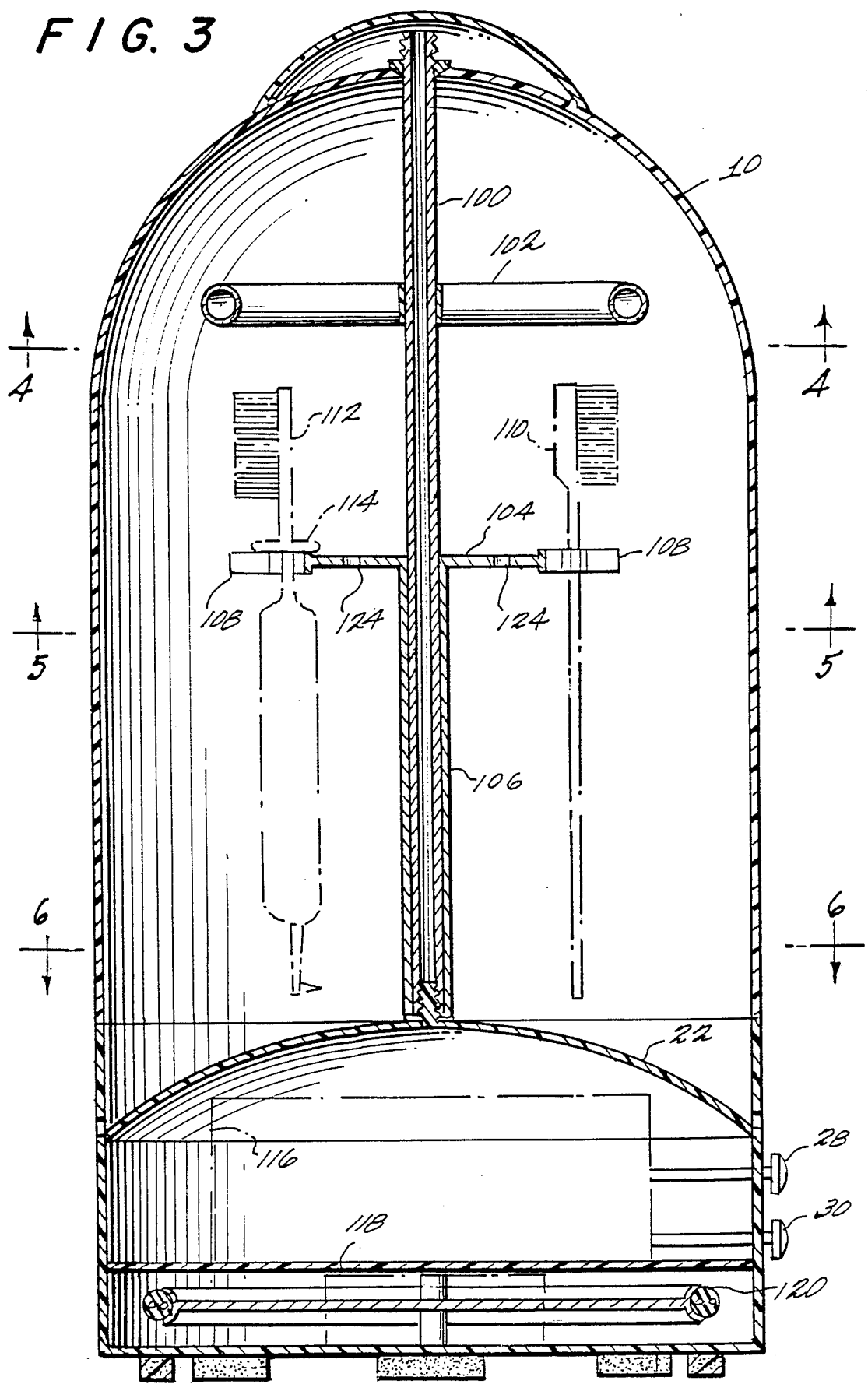

FIG. 8
FIG. 9
FIG. 10
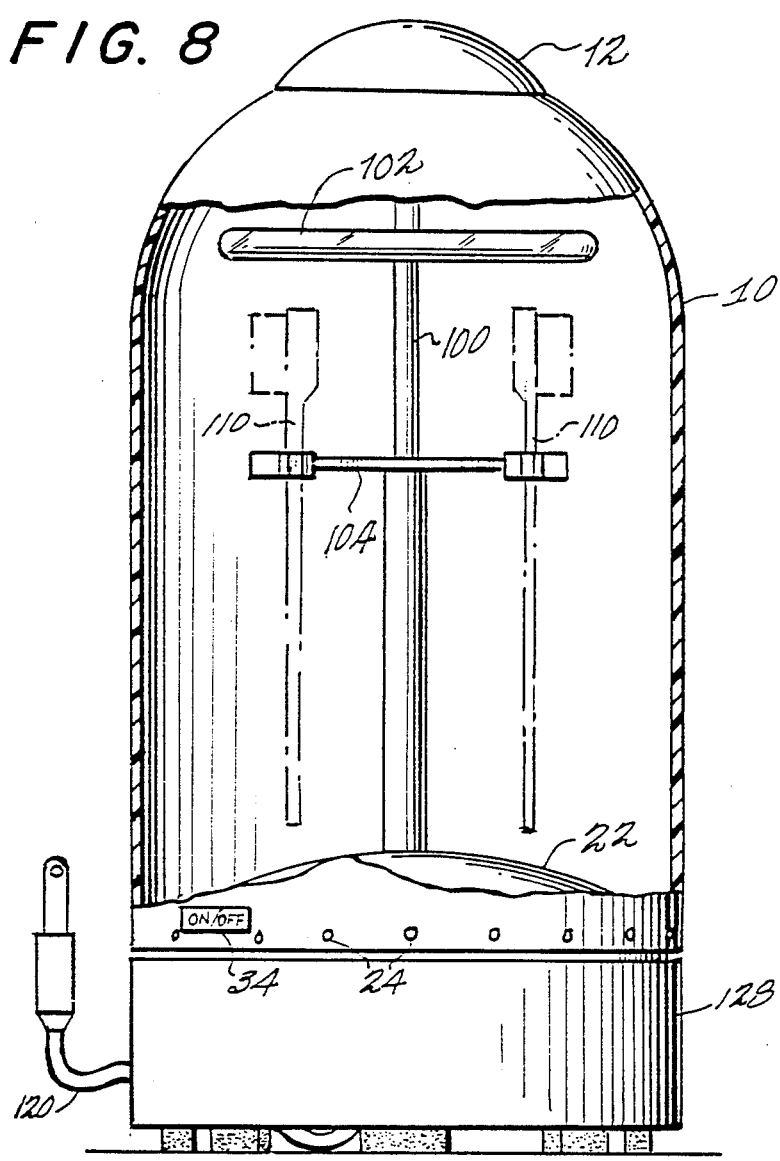
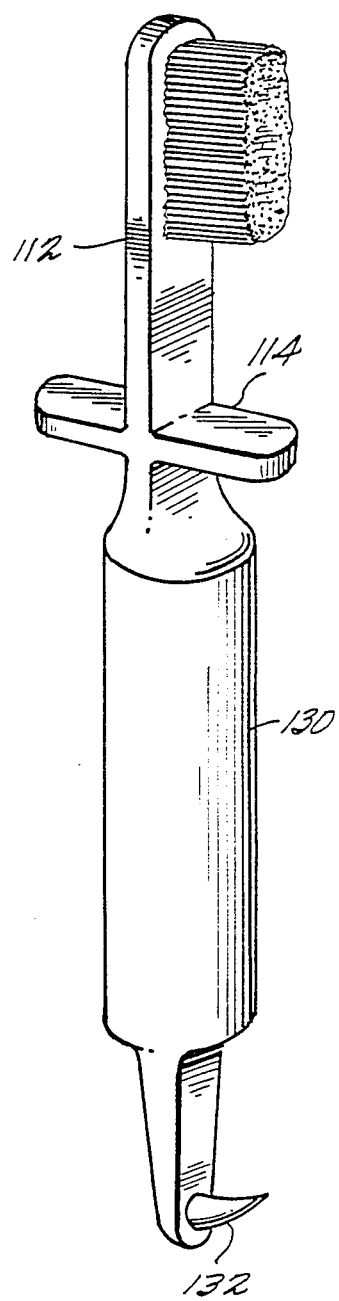
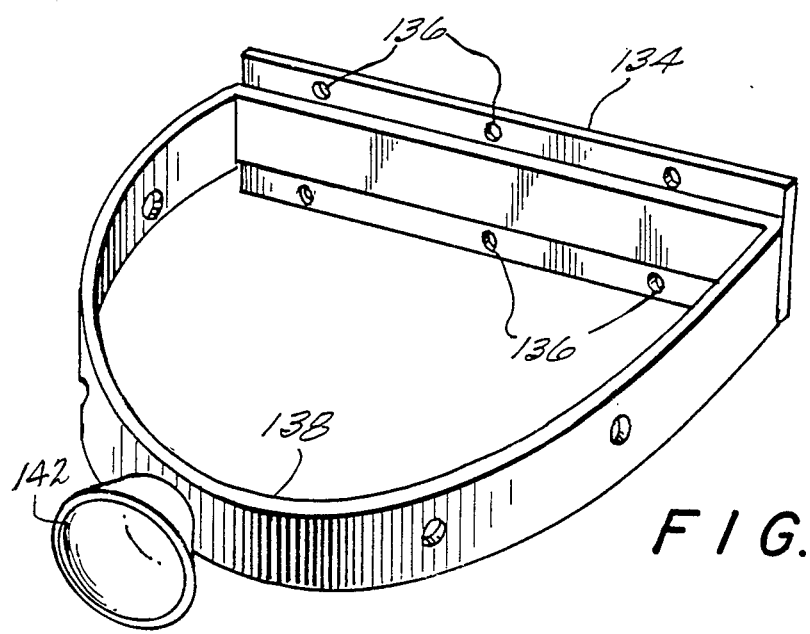

SANITIZER FOR BATHROOM ARTICLES

RELATED APPLICATIONS

This application is a continuation-in-part (CIP) application of U.S. application Ser. No. 721,659 which was filed Apr. 10, 1985.

BACKGROUND OF THE INVENTION

This invention pertains in general to a sanitizer for bathroom articles, and more particularly to a device for housing and sanitizing bathroom articles such as toothbrushes, including the effective draining of drainage fluid from the interior of the sanitizer under the force of gravity.

The existence of a specialized cabinet having a particular germicidal lamp or similar device contained therein for sterilizing bathroom articles placed within the cabinet is a well known concept. The following list of United States patents all relate to the subject of sterilizing bathroom articles.

U.S. Pat. No. 3,955,922—Moulthrop (May, 1976)
U.S Pat. No. 3,820,251—Abernathy (June, 1974)
U.S. Pat. No. 3,776,694—Leittl (December, 1973)
U.S. Pat. No. 3,353,905—Ellis (November, 1967)
U S. Pat. No. 3,309,159—LeSueur et al (March, 1967)
U.S. Pat. No. 2,592,131—Farrar (April, 1952)
U S. Pat. No. 2,579,242—Pask (December, 1951)
U.S. Pat. No. 2,554,156—Rosenthal (May, 1951)
U S. Pat. No. 2,424,036—Jackel (July, 1947)
U.S. Pat. No. 2,356,505—Christensen (August, 1944)

Bathroom articles such as toothbrushes or hair brushes frequently have fluids (e.g., water, saliva, etc.) contained therein after their use which must be drained to obtain proper sterilization and sanitization. Retained water provides fertile breeding ground for unwanted bacteria and other germs. Ultimately, the deadly Legionnaire's Disease outbreak of Philadelphia, Pa. in the 1970's was traced to such breeding in the stagnate portions of a hotel's water system.

The United States patents listed above fall into three categories with respect to drainage of such drainage fluid. The first category includes those that literally make no provision for drainage of the subject fluid, or there is no defined housing from which drainage is necessary. A second category includes devices which have some sort of drainage function, but which is carried out rather ineffectively (i.e., there is no rigorous method to drain all fluids), or in partial dependence upon ventilation. In some instances, constituting a third category, auxiliary means which require a power input are provided to assist with the removal of drainage fluid. For example, in Moulthrop, an electric motor drives a fan to provide forced ventilation over toothbrushes to provide evaporation of drainage fluid. In Abernathy, an electrically powered heating means is used to literally dry the toothbrushes within the housing.

The present invention discloses a device which effectively permits drainage of fluid from toothbrush articles while they are being sanitized within a housing without the necessity of an auxiliary power input.

SUMMARY OF THE INVENTION

One object of the present invention is to provide a device which effectively sterilizes a plurality of bathroom articles, such as toothbrushes. A further object of this invention is to provide effective drainage of drainage fluid from the bathroom articles.

To accomplish these and numerous other objects, a closeable housing is provided having therein a germicidal lamp and a storage rack for holding toothbrushes or similar bathroom articles within the housing. A drainage diaphragm fitted within a bottom portion of the housing is shaped so as to force drainage fluid which falls from the bathroom articles to a peripheral portion of the housing. Drainage holes may be associated with this peripheral portion of the housing to permit passage of the drainage fluid from the housing as directed thereto by the drainage diaphragm.

The housing of the present invention may be generally cylindrical in shape. In one embodiment, the housing has a domed top and a relatively flat bottom. In another embodiment, the top is not domed. A portion of the housing, such as, for example, the domed top in one embodiment may be partially transparent so as to permit light from the germicidal lamp to also function as a night light. The cylindrical housing may have a curved, hinged or sliding door to permit access to the interior of the housing. Toothbrushes or the like may be mounted on a plate, which in one embodiment is arranged so a to enable it to revolve, having spring clips about its periphery. This plate may also have holes therein to permit drainage of fluid from the bathroom articles downward under the force of gravity towards the drainage diaphragm.

The drainage diaphragm is curved downward (i.e., concave in the direction of gravity) to permit the force of gravity to direct precipitating drainage fluid towards the periphery of the housing. Drainage holes lining the periphery of the housing immediately above the plane formed by the intersection of the housing and the diaphragm permits this precipitated and directed drainage fluid to be removed from the interior of the housing.

The drainage diaphragm also serves to seal off an even lower portion of the housing from the drainage fluid. This function permits installation of adjunct self-contained electrical appliances within the lower portion of the housing in one embodiment. In another embodiment, the electrical appliances are mounted in an upper portion of the housing. These appliances may include electrical devices such as a radio and/or an electric clock. In the embodiment wherein the electrical appliances are mounted in the lower portion of the housing, knobs and control elements of such electrical appliances may be protruded through this base portion of the housing. In the other embodiment, the knobs and control elements protrude through the upper portion of the housing.

Further, feet may be mounted on the bottom of the housing itself to permit sound from a speaker formed in the bottom of the housing to be emitted in conjunction with operation of an adjunct installed radio, etc.

The particular spring clips of the revolving plate of this invention may be used in conjunction with custom tooth-brushes which have registration elements emerging from the normally smooth handles thereof to permit the head of such tooth-brushes to be held in predetermined relationship with the revolving plate. This function permits the bristles of the toothbrushes to be isolated from surfaces foreign to the bristle mount itself.

The present invention also includes a further embodiment wherein the adjunct electrical devices housed beneath the concave diaphragm include a rechargeable battery for powering the germicidal lamp. The base of such an embodiment is further adapted to be mated with a rechargeable base unit for recharging the rechargeable battery. The resulting sanitizing device is a portable apparatus capable of performing the sanitizing, night light and drainage features of the present invention.

The present invention also further encompasses the inclusion of mounting means on the housing bodies of the various present embodiments to permit selective mounting of those bodies on a surface, such as a bathroom or kitchen wall.

The foregoing summary of the invention offers but an incomplete listing of some of the more important features and aspects of the present invention. A more complete understanding and appreciation of the features of this invention may be understood by studying the accompanying figures and the following disclosure.

BRIEF DESCRIPTION OF THE DRAWINGS

Concepts and features of the presently preferred embodiments of this invention may be better understood with reference to the following figures, in which:

FIG. 1 is a front elevation of a first embodiment of a bathroom article sanitizer in accordance with the principles of the present invention;

FIG. 2 is a side elevation of the sanitizer shown in FIG. 1;

FIG. 3 is a longitudinal section through the center of the sanitizer shown in FIG. 1;

FIGS. 4 through 6 are cross-sections taken at various levels in other figures as indicated;

FIG. 7 is a base plan of the FIG. 1 embodiment;

FIG. 8 is an elevational view with parts thereof in section of a second embodiment of a device in accordance with the present invention which constitutes a portable (i.e., rechargeable battery-powered) version thereof;

FIG. 9 illustrates a custom toothbrush having a registration element for use with any of the embodiments set forth herein;

FIG. 10 illustrates a perspective view of mounting arrangement for use with any of the embodiments;

DETAILED DESCRIPTIONS OF THE VARIOUS SPECIFIC EMBODIMENTS

Figure 11:
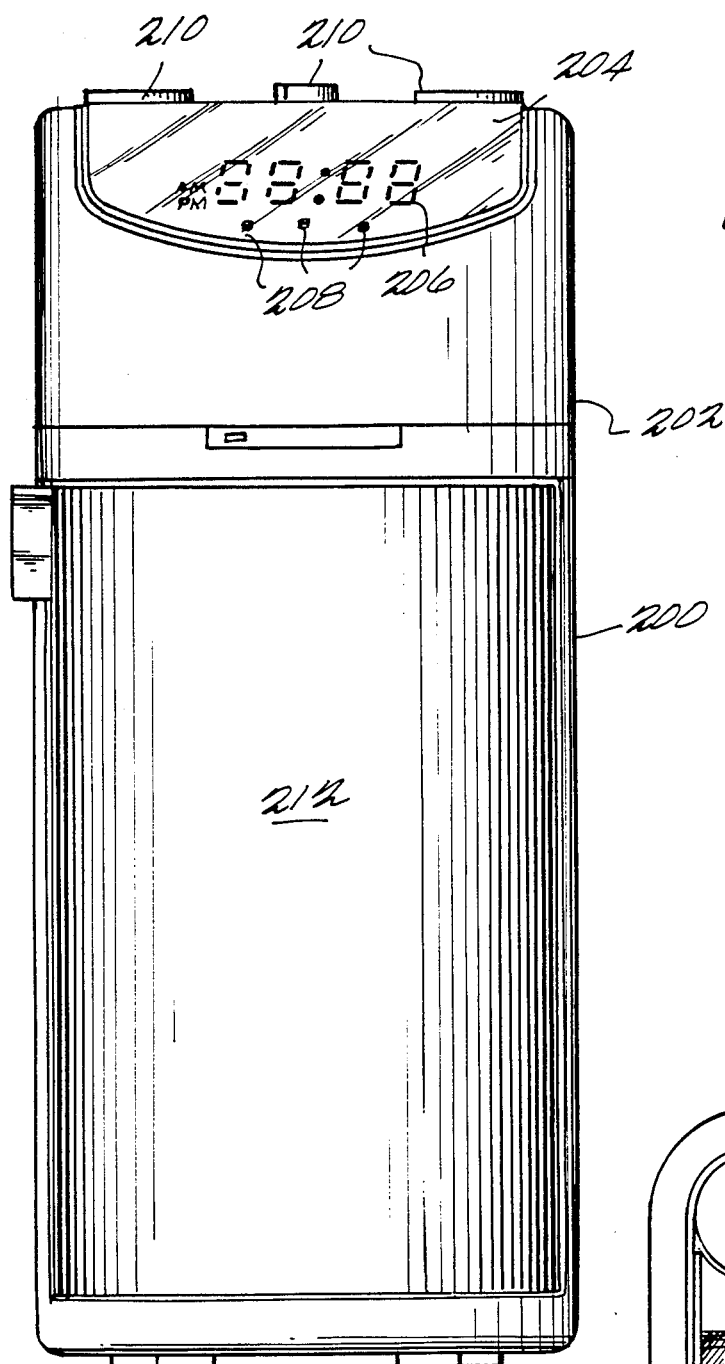
FIG. 11 is a front view of the presently preferred exemplary embodiment of a sanitizer in accordance with the principles of the present invention.

FIG. 1 is a front elevation of a first embodiment of a sanitizer for bathroom articles in accordance with the principles of the present invention. A cylindrical housing is defined by cover 10. This cover may include a frosted plexiglas material, or of other suitable material. Cylindrical housing 10 has an upper portion 12 which may be transparent plastic to permit light from a germicidal lamp contained within the housing to pass from the housing, thereby accomplishing a night light function. A door 14 permits selective closing and opening of the housing 10 to permit placement and retrieval of bathroom articles. Door 14 has hinges 16 and 18 and doorknob 20, which function in a conventional manner.

Reference character 22 points to a dotted line representation of a drainage diaphragm contained within the housing 10. In accordance with the present invention, drainage fluid associated with the bathroom articles stored within the housing 10 precipitates onto the drainage diaphragm 22 by the force of gravity. Since diaphragm 22 is concave-shaped in the direction of gravity and blocks all possible downward paths of the fluid, all such precipitated drainage fluid is directed toward the periphery of the housing 10. At such peripheral portions of the housing 10 are located a plurality of drainage holes 24 to permit drainage of this fluid from within the housing. The drainage diaphragm 22 and plurality of drainage holes 24 constitute a drainage means for venting by the force of gravity drainage fluid from the interior of the housing through a peripheral base portion of the housing 10.

Drainage diaphragm 22 seals off all portions within the housing below the diaphragm from drainage fluid. Therefore, adjunct self-contained electrical devices may be safely incorporated into this further base portion of the housing 10 beneath the diaphragm 22. For example, 26 is a face plate or display for a radio device, with knobs 28 and 30 operating the same. Reference character 32 refers to a display for a digital or electronic clock. Switch 34 may control the germicidal lamp contained within the housing 10, discussed further below. Rubber cushion pads 36 may be placed on the bottom of housing 10 to provide non-skid footing for the sanitizer and to permit sound to emerge from a speaker mounted in the bottom of housing 10. This is discussed further below.

Although various physical dimensions may be applied to the embodiment of FIG. 1 in accordance with the present invention, this exemplary embodiment is drawn roughly to scale for a six inch diameter thereof, with a total height of twelve inches from the lowermost tip of rubber cushion pads 36 to the uppermost tip of transparent dome 12.

FIG. 2 is a side elevation of the device shown in FIG. 1. Throughout this application, like reference numerals among figures refer to the same or analogous elements thereof. Hence, reference character 12 again refers to the transparent dome top of housing 10. Diaphragm 22 is again shown in dotted line since it is contained within housing 10, and drainage holes 24 are shown to continue around the total periphery of the housing 10. Control knobs 28 and 30, and display segments 26 and 32 are associated with an adjunct radio and electric clock, as in FIG. 1. Rubber feet 36 are all of identical size and shape, but only appear of different sizes due to the changing perspective thereof brought on by rotation of the figure. Base plan FIG. 7, discussed below, clearly shows that rubber cushion feet 36 are identical with respect to each other. Reference characters 138 and 142 refer to a mounting means for the present invention, discussed further below with regard to FIG. 10.

FIG. 3 is a longitudinal section of the embodiment shown in FIGS. 1 and 2 along the center thereof. Section markers for FIGS. 4–6 refer to the sections represented by FIGS. 4 through 6, respectively.

Reference character 100 refers to an upright post mounted within the housing 10, which is threaded at both of its ends so as to be fixedly mounted within the housing. The upright post 100 in turn serves as an element for mounting the germicidal lamp 102 and revolving plate 104. In this embodiment, the germicidal lamp 102 comprises a circular fluorescent ultraviolet light, but other known germicidal lamps are freely substitutable with this element. Details of the mounting of germicidal lamp 102 on upright post 100 is shown and discussed further below.

The bottom end of upright post 100 deadends into the upper surface of diaphragm 22. Tube 106 surrounds upright post 100 between the upper surface of diaphragm 22 and the lower surface of revolving plate 104. The revolving plate 104 may be fixed to the upper end of tube 106, and ball bearings may be employed between upright post 100 and tube 106 so as to provide free circular movement for revolving plate 104 around an axis defined by post 100.

Spring clips 108 are mounted around the periphery of revolving plate 104 so as to receive and hold inserted bathroom articles. Holes 124 are drainage passages, discussed further below with regard to FIG. 5. By way of example only, the spring clip holders 108 of FIG. 3 have contained therein toothbrushes. Toothbrush 110 is a conventional style toothbrush which is locked into place by the spring force which is inherent in the spring clip 108. Toothbrush 112 is a toothbrush modified in accordance with the present invention so as to have registration elements 114 protruding from the handle thereof so as to ensure that the bristles of toothbrush 112 remain out of contact with the spring clip 108. Such contact could occur if the toothbrush 112 were to slide downward under the force of gravity towards spring clip 108 until the brushes of toothbrush 112 actually touched spring clip 108. Inasmuch as one of the chief functions and objects of the present invention is to sanitize bathroom articles, the registration element 114 of toothbrush 112 furthers this purpose by physically isolating the bristles of toothbrush 112 from foreign surfaces other than the actual mounting portion of toothbrush 112.

Cavity 116 may house the workings of an electric radio which uses window 26 as a display. Control knobs 28 and 30 are again illustrated to show their cooperation with cavity 116. Cavity 118 may be used for housing the functional elements of an electric clock, etc., which utilizes window 32 as a display therefor.

Reference character 120 refers to a retractable AC power cord (shown further, below) which may be used to provide power from a conventional AC power source to the various electrical devices of an apparatus in accordance with the present invention, including the germicidal lamp 102, a radio contained within cavity 116 and an electric clock contained in cavity 118.

The revolving plate 104, peripheral spring clips 108 and tube 106 with its ball bearings may constitute storing means for storing bathroom articles (such as toothbrushes) within the housing 10. While the longitudinal sectional view apparently shows only two such peripheral spring clips 108, different numbers of such peripheral spring clips may be used in accordance with the present invention. Hence, different numbers of bathroom articles such as toothbrushes or a mix of different articles may be stored within an apparatus in accordance with the present invention. As discussed further below, FIG. 5 discloses an embodiment having six such peripheral spring clips 108, while FIG. 8 discloses an embodiment having only two such peripheral spring clips 108.

FIGS. 4 through 6 show three respective cross-sections as indicated in FIG. 3. The sectional lines of FIGS. 4 through 6 illustrate the longitudinal section orientation of FIG. 3.

FIG. 4 illustrates a sectional line of FIG. 3 as indicated, looking upward therefrom. Upright post 100 is shown as a small circular part in the center of the cross-section. The germicidal lamp 102 is shown as a concentric circular element surrounding the shaft 100. As stated before, this particular preferred embodiment illustrates the germicidal lamp as being a circular fluorescent tube emitting light in the ultraviolet range, but other suitable equivalents are permitted. Cross member 122 supports the germicidal lamp 102.

FIG. 5 illustrates the indicated cross-section in FIG. 3, also looking upward. Revolving plate 104 is shown as a circular plate having drainage passages 124 therein. These drainage passages permit drainage fluids to flow from toothbrushes mounted in peripheral spring clips 108 (shown as six in number in this embodiment) downward to diaphragm 22. Under the force of gravity, diaphragm 22 then directs the precipitated drainage fluid towards the periphery of housing 10, as discussed above. Rotating plate 104 is concentric with the upright mounting shaft 100. In FIG. 5, shown at the periphery of housing 10 is the doorknob 20 of door 14.

FIG. 6 illustrates a cross-section taken along the indicated line of FIG. 3, which looks downward therefrom. Cavities 116 and 188 are shown as they are located within the housing 10. Control knob 28 associated with cavity 116 is illustrated, but control knob 30 which appears directly below knob 28 is not illustrated since it is blocked from view. Shaft 100 is again centrally located in the cross-section. Retractable AC power cord 120 winds around in a circular fashion within housing 10 as shown.

FIG. 7 illustrates a base plan of the housing 10 of FIG. 1 (i.e., looking at only the bottom of the housing). As discussed above, cushion pads 36 are all identical in nature and located symmetrically around the center of housing 10. Also shown in FIG. 7 is one exemplary embodiment of audio holes 126 formed in the bottom of the housing 10 to permit sound from a speaker contained therein to emerge to a listener. Any suitable pattern may be used, as is true for the configuration of cushion pads 36, and the FIG. 7 illustration is exemplary only and not intended to limit the present invention. Also shown are control knob 30, door knob 20 and power cord 120.

FIG. 8 illustrates a second embodiment of the present invention which is "portable" in that it has a rechargeable battery contained within the base of housing 10 beneath the diaphragm 22. The base of housing 10 is adapted to mate with a rechargeable base unit 128 for recharging the enclosed battery. Details of such a battery recharging system are well known and need not be repeated here. That portion of the sanitizer above base portion 128 may then be detached and taken along as a portable unit for traveling with the user. The physical dimensions of the FIG. 8 embodiment may typically be smaller than that of the FIG. 1 embodiment, and hence the revolving plate 104 may be limited in size so as to support or house only two toothbrushes 110 and 112, or other similar bathroom articles. As before, germicidal lamp 102 sanitizes the bathroom articles placed in the peripheral clips of revolving plate 104, which revolves around upright shaft 100. Drainage diaphragm 22 and peripheral drainage holes 24 function as before to vent by the force of gravity any drainage fluid from within the housing 10.

FIG. 9 shows an exemplary embodiment of the toothbrush 112 usable with the embodiments of FIGS. 1 and 8, having registration elements 114 to suitably hold the bristles of tooth-brush 112 a predefined distance separate from the peripheral spring clamps 108 of revolving plate 104. This particular embodiment shown in FIG. 9 also includes an enlarged handle portion 130 for easier manipulation of the toothbrush, and an elongated tip (rubberized) 132 for easy removal of large food particles from between teeth. The toothbrush of FIG. 9 is part of and furthers the objects of the present invention in that it utilizes its registration element feature to further the sanitization effects of the various embodiments of the sanitizer. As discussed before, elements 114 serve to register (or separate) the bristles of toothbrush 112 from any foreign surfaces (i.e. surfaces other than the mounting portions of toothbrush 112 for the bristles).

FIG. 10 illustrates a perspective view of a mounting means for the present invention. Element 134 defines a wall bracket which is suitably attached by elements (e.g., a plurality of screws 136) to a desired surface, such as a bathroom or kitchen wall. Wall bracket 134 has a semi-circular extension piece 138 which is integrally attached thereto and extends therefrom. Extension piece 138 has contained therein various select holes 140 for variably mounting a suction cup 142 or similar device therein. The holes 140 (shown as 5 in the exemplary embodiment of FIG. 10, but which may be other in number) are threaded to receive a threaded base portion of suction cup 142. Other methods of mounting, such as a bayonet mount, are possible in place of the screw mount. The suction cup 142 may be formed of rubber, with the threaded base portion thereof being hardened rubber. The suction cup 142 is then attached to a desired portion of housing 10, and its threaded end associated with a desired one of holes 140. The wall bracket 134 is affixed to the desired surface with elements 136, and the result is selective and desired fixation of a sanitizer in accordance with the present invention to a suitable surface.

FIG. 11 is a front view of the presently preferred exemplary embodiment of a sanitizer in accordance with the principles of the present invention. Each part or element of this embodiment will not be described in detail because most of the parts are analogous to those of the embodiments shown in FIGS. 1-10. Although the same general principles of the FIGS. 1-10 embodiments are utilized in the FIGS. 11-15 embodiment, the overall structure of this preferred embodiment is somewhat different.

This embodiment includes a housing 200 that is generally cylindrical in shape. However, this embodiment does not have a domed-top portion. Rather, this embodiment includes the electrical appliances such as clock and radio in an upper portion 202 of housing 200. A display panel 204 includes a clock/radio controlled display 206 and control elements 208 and 210.

In this embodiment, the door 212 is not hinged as in the FIGS. 1-10 embodiment. Rather, it pivots about two portions along a central axis of housing 200.

Figure 12:
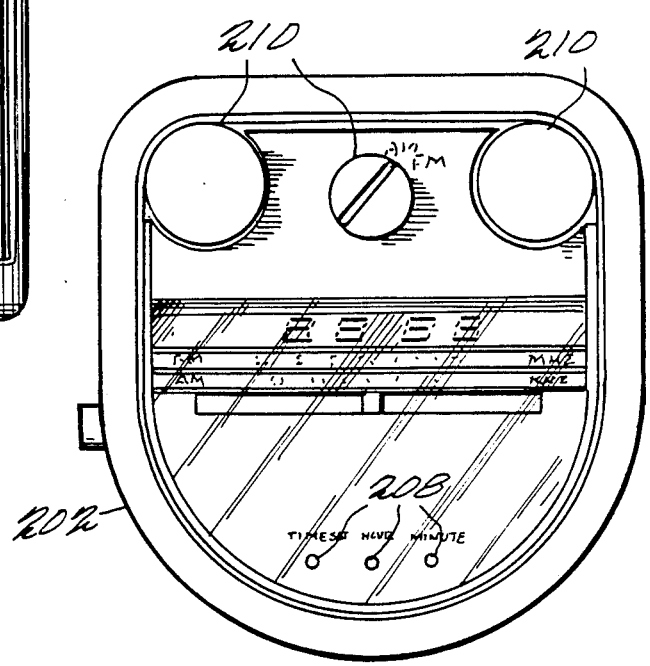
FIG. 12 is a top view of the sanitizer shown in front view in FIG. 11.

FIG. 12 is a top view of the sanitizer shown in front view in FIG. 11. Control elements 210 are preferably knobs that can be easily manipulated by the user to control the electrical appliances. For example, control elements 210 might tune the radio, set the clock, etc.

Figure 13:
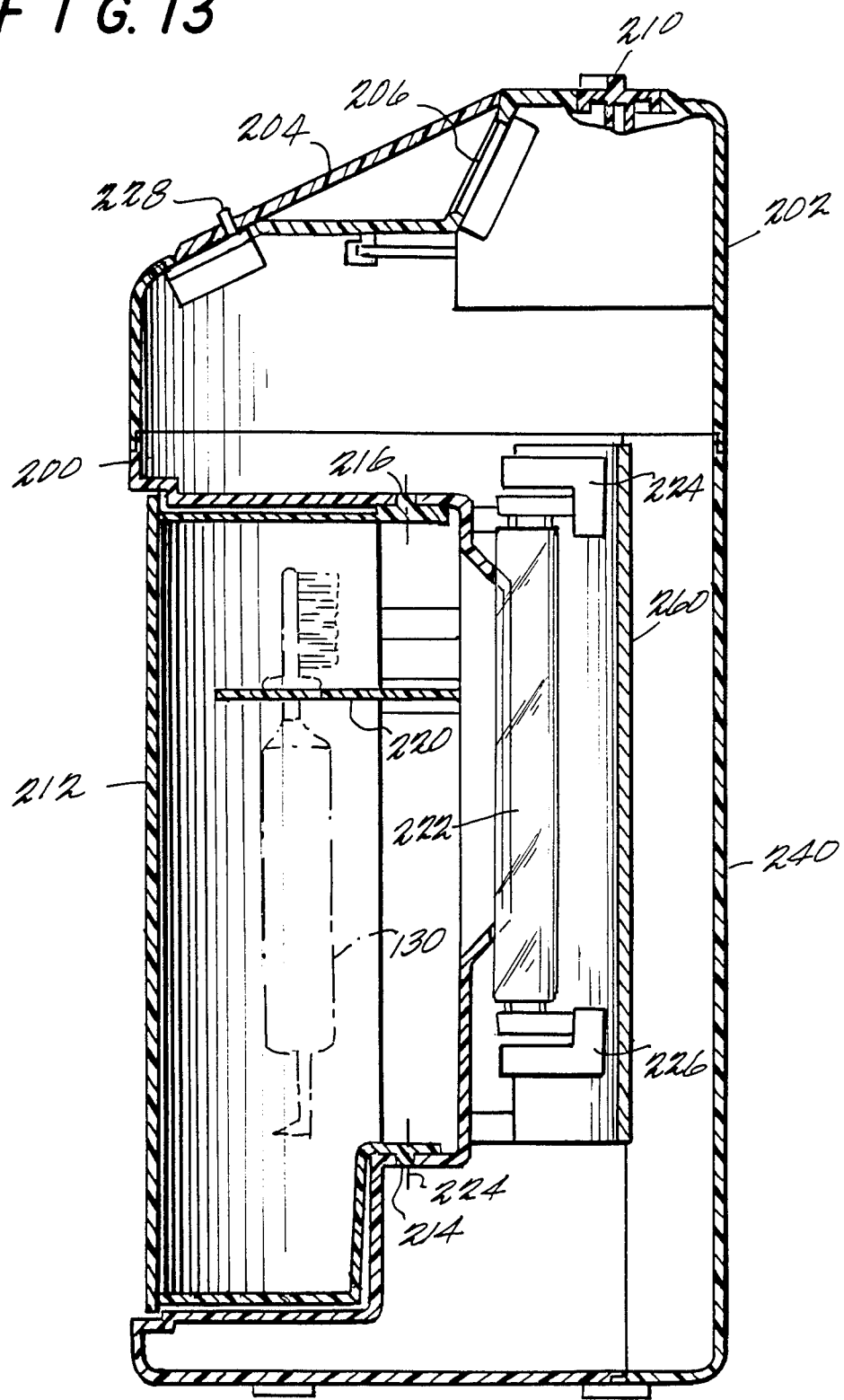
FIG. 13 is a cutawayt side view of the embodiment shown in FIG. 11.

FIG. 13 is a cutaway side view of the embodiment shown in FIG. 11. In this FIGURE, one can see how door 212 pivots at points 214 and 216, roughly along the central axis of housing 200. Toothbrushes 130 are mounted on a rack 220 and are exposed to the action of a germicidal light 222. Germicidal light 222 is mounted in mounting portions 224 and 226 which support in a generally vertical position. A reflector 260 is provided to reflect light from germicidal light 222 toward the articles being sanitized. Reflector 260 can also be seen clearly in FIG. 14. Housing 200 has a removable back portion 240.

Figure 14:
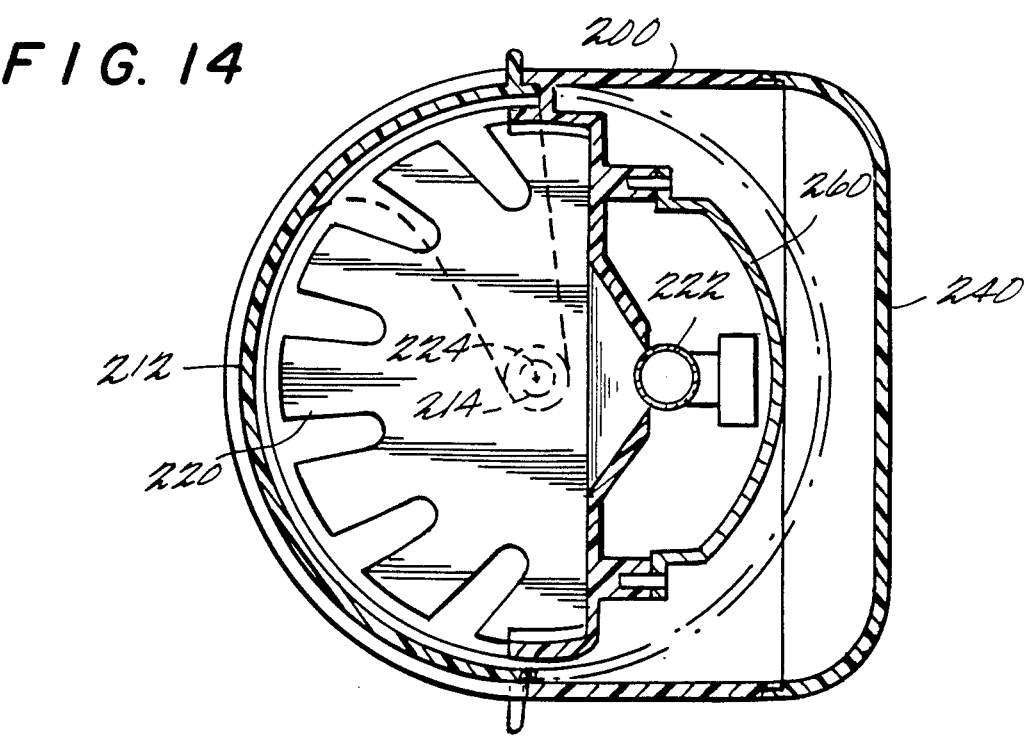
FIG. 14 is a cutaway top view of the sanitizer shown in FIG. 11 which more clearly shows the configuration of rack 220 for holding the toothbrushes.

FIG. 14 is a cutaway top view of the sanitizer shown in FIG. 11 which more clearly shows the configuration of rack 220 for holding the toothbrushes. The central axis about which door 212 pivots is indicated by reference numeral 224.

Figure 15:
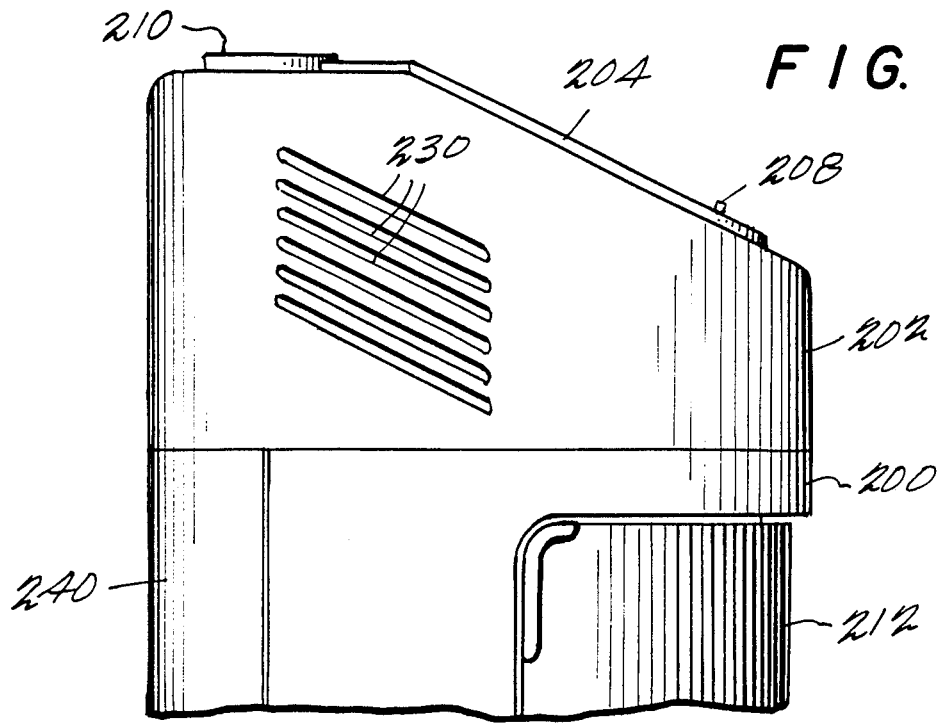
FIG. 15 is a side view of the upper portion 202 of housing 200.

FIG. 15 is a side view of the upper portion 202 of housing 200. As shown, upper portion 202 includes vents 230 for allowing heat from germicidal lamp 222 to escape.

Many further modifications and variations of the present invention are possible within the skill of one of ordinary skill in the art. For example, the germicidal lamp 102 may be any other known germicidal lamp other than an ultraviolet fluorescent circular tube. Also, any of the materials used in producing the present apparatus may be appropriately plastic, rubber, metal, etc. in accordance with particular design and aesthetic needs. Also, housing 10 need not be strictly limited to a cylindrical shape, but might be other shapes such as rectangular or triangular, with the diaphragm 22 suitably adapted to have its outer peripheral portion lie flush with the inner walls of the particular housing. Peripheral holes 24 may then be suitably located around the periphery of the particular shape of the housing so as to drain off precipitated drainage fluid directed thereto by the diaphragm 22. Other adjunct electrical devices such as transceivers, calculators or televisions may be included in the base portion of the housing 10 beneath the protective diaphragm 22. All such modifications and variations which would occur to one of ordinary skill in the art are intended to be included within the scope of the present invention, which is further defined by the appended claims.

What is claimed is:

1. A sanitizer for bathroom articles, comprising:
   a closeable housing wherein said housing comprises a cylindrical body, a flat bottom, and a door;
   storing means for storing at least one bathroom article in said housing;
   sanitizing means for sanitizing the stored bathroom article; and
   drainage means for venting by the force of gravity drainage fluid from the interior of said housing through a peripheral base portion of said housing.

2. A sanitizer as in claim 1, wherein
   said sanitizing means comprises a germicidal lamp housed within said housing; and
   said cylindrical body has transparent portions to emit light from said housing produced by said lamp.

3. A sanitizer as in claim 2, wherein said germicidal lamp comprises an ultraviolet light fixture.

4. A sanitizer as in claim 1 wherein said storing means comprises a revolving circular plate mounted within said housing, said plate having peripheral clips for receiving and holding the bathroom articles to be stored, wherein said clips are at least two in number.

5. A sanitizer as in claim 4, wherein said clips are at least 6 in number.

6. A sanitizer as in claim 1, wherein said drainage means comprises a cupped diaphragm located beneath said storing means within said housing, said diaphragm being concave downward with respect to gravity and having its outer rim everywhere in contact with said housing so as to seal off a bottom portion thereof from drainage fluid, and said housing has included therein drainage holes in its peripheral base portion for passing from said housing drainage fluid directed thereto by said diaphragm.

7. A sanitizer as in claim 6, wherein said bottom portion of said housing has a plurality of cavities therein for housing adjunct self-contained electrical appliances such as a radio and clock with their associated control knobs exposed through to the exterior of said housing, and said bottom portion retains a retractable power cord adapted to supply necessary electric power to electrical appliances contained within said housing, including said sanitizing means.

8. A sanitizer as in claim 7, wherein said housing has raised feed on the bottom thereof and a speaker housed therein, said speaker being associated with said adjunct electrical appliances.

9. A sanitizer as in claim 1, wherein said storing means and said sanitizing means are mounted on a common upright post within said housing, with said sanitizing means being above said storing means with respect to gravity.

10. A sanitizer as in claim 4, wherein said circular plate has drainage passages therein to permit drainage fluid from stored bathroom articles to pass therethrough under the force of gravity.

11. A sanitizer as in claim 2, further comprising adjustable mounting means for selectively mounting said housing on a desired surface.

12. A sanitizer as in claim 3, wherein said housing has a bottom portion thereof which has a rechargeably battery for powering said sanitizing means, and said bottom portion is adapted to mate with a recharging base stand so as to recharge said rechargeable battery.

13. A device for housing and sanitizing bathroom articles, comprising:
a cylindrical body with a closeable door;
a storage rack mounted within said body for receiving bathroom articles;
a germicidal lamp mounted within said body for sanitizing received bathroom articles;
an upright support post for said rack and said lamp to be mounted thereon within said body, with said lamp being mounted above said rack; and
a curved drainage diaphragm in a bottom portion of said body for directing under the force of gravity drainage fluid from received bathroom articles to the periphery of said body,
drainage holes being formed in the periphery of said body for passing drainage fluids from said body directed thereto by said drainage diaphragm.

14. A device according to claim 13 wherein at least a portion of said body is made of such a material to pass at least a portion of light generated by said germicidal lamp.

15. A device as in claim 13, wherein said body further comprises a transparent domed top to emit light therefrom produced by said germicidal lamp, thereby constituting a night light.

16. A device as in claim 13, wherein said body has contained in a base portion thereof beneath said diaphragm a radio and an electric clock, which are sealed off from drainage fluid by said diaphragm.

17. A device according to claim 13 wherein said body has contained therein a radio and an electric clock.

18. A device as in claim 13, further comprising means for selectively mounting said body on a desired surface.

19. A device as in claim 14, further comprising means for selectively mounting said body on a desired surface.

20. A toothbrush sanitizer, comprising:
a closeable housing;
storing means for storing at least one toothbrush in said housing;
sanitizing means for sanitizing said toothbrush; and
drainage means for venting by the force of gravity drainage fluid from the interior of said housing through a peripheral base portion of said housing.

21. A sanitizer as in claim 20, wherein said toothbrush includes registration means for securing said toothbrush in said storing means in a predefined relationship therewith to prevent bristles of said toothbrush from contacting foreign surfaces.

22. A toothbrush sanitizer, comprising:
a cylindrical body with a closeable door;
a storage rack mounted within said body for receiving a toothbrush;
a germicidal lamp mounted within said body for sanitizing received toothbrushes;
an upright support post for said rack and said lamp to be mounted thereon within said body, with said lamp being mounted above said rack; and
a curved drainage diaphragm in a bottom portion of said body for directing under the force of gravity drainage fluid from received toothbrushes to the periphery of said body,
drainage holes being formed in the periphery of said body for passing drainage fluids from said body directed thereto by said drainage diaphragm.

23. A toothbrush sanitizer, comprising:
a cylindrical body with a closeable door, at least a portion of said body being made of such a material to pass at least a portion of light generated by a germicidal lamp;
a storage rack mounted within said body for receiving at least one toothbrush;
a germicidal lamp mounted within said body for sanitizing received toothbrushes;
an upright support post for said rack and said lamp to be mounted thereon within said body, with said lamp being mounted above said rack; and
a curved drainage diaphragm in a bottom portion of said body for directing under the force of gravity drainage fluid from received toothbrushes to the periphery of said body,
drainage holes being formed in the periphery of said body for passing drainage fluids from said body directed thereto by said drainage diaphragm.

* * * * *